(12) United States Patent
Kang et al.

(10) Patent No.: US 8,236,549 B2
(45) Date of Patent: Aug. 7, 2012

(54) BACILLUS AMYLOLLQUEFACIENS STRAIN

(75) Inventors: Yaowei Kang, Christiansburg, VA (US);
Shawn Semones, Salem, VA (US);
Jessica Smith, Roanoke, VA (US);
Michael Frodyma, Saskatoon (CA)

(73) Assignee: Novozymes Biologicals, Inc., Salem, VA (US)

( * ) Notice: Subject to any disclaimer, the term of this patent is extended or adjusted under 35 U.S.C. 154(b) by 0 days.

(21) Appl. No.: 13/099,717

(22) Filed: May 3, 2011

(65) Prior Publication Data

US 2011/0274673 A1 Nov. 10, 2011

Related U.S. Application Data

(60) Provisional application No. 61/331,203, filed on May 4, 2010.

(51) Int. Cl.
*A01N 63/00* (2006.01)
*C12N 1/20* (2006.01)

(52) U.S. Cl. .................. 435/252.5; 435/832; 424/93.46

(58) Field of Classification Search .................. None
See application file for complete search history.

(56) References Cited

U.S. PATENT DOCUMENTS

| 5,494,809 | A | 2/1996 | Tanaka | |
|---|---|---|---|---|
| 6,589,524 | B1 * | 7/2003 | Douillet | .................. 424/93.462 |
| 6,960,342 | B2 | 11/2005 | Wu | |
| 2004/0052776 | A1 | 3/2004 | Wu | |
| 2008/0102062 | A1 | 5/2008 | Kim | |
| 2009/0324533 | A1 | 12/2009 | Snyder | |
| 2010/0015081 | A1 | 1/2010 | Drahos | |
| 2010/0028314 | A1 | 2/2010 | Snyder | |

FOREIGN PATENT DOCUMENTS

WO    WO 2005/059112    6/2005

OTHER PUBLICATIONS

Abate et al., "Production of amylolytic enzymes by *Bacillus amyloliquefaciens* in pure culture and in co-culture with *Zymomonas mobilis*", Biotechology Letters, vol. 21, pp. 249-252 (1999).
Correa et al., "*Bacillus amyloliquefaciens* BNM122, a potential microbial biocontrol agent applied on soybean seeds, causes a minor impact on rhizosphere and soil microbial communities", Applied Soil Ecology, vol. 41, pp. 185-194 (2009).
Priest et al., "*Bacillus amyloliquefaciens* sp. nov. norn. rev.", International Journal of Systematic Bacteriology, vol. 37, pp. 69-71 (1987).
Sietske De Boor et al., "On the safety of *Bacillus subtilis* and *B. amyloliquefaciens*: a review", Applied Microbiology Biotechnology, vol. 361, pp. 1-4 (1991).
Moliszewska et al., "Activity of Bacteria Strains Originated from Sewage Sludge Against Some Soil Fungi", Japanese Society of Soil Science and Plant Nutrition, vol. 50, No. 6, pp. 807-814 (2004).

* cited by examiner

*Primary Examiner* — Vera Afremova
(74) *Attorney, Agent, or Firm* — Thomas C. Sova, IV

(57) ABSTRACT

The present disclosure relates to a strain of *Bacillus amyloliquefaciens* bacteria that hyperproduces amylase enzyme and protease enzyme. The strain is also suitable for producing lipase for the degradation of oleaginous materials such as fats, greases and cooking oils. The strain also has excellent fungicidal and/or fungistatic qualities. The strain of the present disclosure and the enzymes produced thereby have a number of applications, including agricultural uses, laundry and dish detergents, drain cleaners and spot removers, and among other things, baking applications.

9 Claims, 4 Drawing Sheets

BACILLUS AMYLOLLQUEFACIENS STRAIN

CROSS-REFERENCE TO RELATED APPLICATIONS

This application claims the benefit under 35 U.S.C. 119 of U.S. provisional application No. 61/331,203 filed May 4, 2010, the contents of which are fully incorporated herein by reference.

CROSS-REFERENCE TO DEPOSITED MICROORGANISMS

The present disclosure refers to deposited microorganisms. The contents of the deposited microorganisms are fully incorporated herein by reference.

FIELD OF THE INVENTION

The present disclosure relates to *Bacillus amyloliquefaciens* strain NRRL B-50350. The strain is characterized as *Bacillus* bacteria having excellent amylase, surfactant and antifungal activity. Further, the strain of the present disclosure produces multiple useful enzymes and has lipase activity, phage resistance, and high tolerance to pH, salt, and temperature. The *Bacillus amyloliquefaciens* strain of the present disclosure and enzymes it produces has a number of applications in the areas of agriculture production, detergent industry, bio-ethanol industry, and the baking industry.

BACKGROUND OF THE INVENTION

*Bacillus amyloliquefaciens* or *B. amyloliquefaciens* is a well known aerobic bacteria often found in soil samples that is responsible for much of the world's production of alpha amylase and protease. *B. amyloliquefaciens* is a Gram-positive, motile, rod-shaped bacterium which often forms chains. The optimal temperature for growth is 30 to 40° C., with no growth below 15° C. or above 50° C. The organism was previously described and distinguished from *B. subtilis* in Priest, et al., *Bacillus amyloliquefaciens sp. nov., nom. rev., International Journal of Systematic Bacteriology*, 37, 69-71 (1987) (herein incorporated by reference in its entirety). The organism has also been characterized as a low G+C organism.

It has been suggested that a strain of *B. amyloliquefaciens*, BNM122, could be a promising ecological alternative to chemical agricultural treatments and be used to develop a sustainable agricultural management to either replace or reduce agrochemical use and/or abuse. For examples, one study reported the use of *B. amyloliquefaciens* as a microbial biocontrol agent (MBCA) characterized as an environmentally friendly alternative to reduce or replace the chemical control of plant diseases. See, e.g., Correa et al, *Bacillus amyloliquefaciens BNM122, a potential microbial biocontrol agent applied on soybean seeds, causes a minor impact on rhizosphere and soil microbial communities, Applied Soil Ecology* 41, 185-194 (2009) (herein incorporated by reference in its entirety). Here, a strain of *B. amyloliquefaciens* was shown to colonize seeds and roots when applied as a coating on seeds to, inter alia, control soil-borne fungal pathogens.

One strain of *B. amyloliquefaciens*, MIR-41, has also been described as an alpha-amylase hyperproducer. This strain has been used in combination with other microbes to produce ethanol from starch substrates. See for example, Abate, et al., *Production of amylolytic enzymes by Bacillus amyloliquefaciens in pure culture and in co-culture with Zymomonas mobilis, Biotechnology Letters* 21, 249-252 (1999) (herein incorporated by reference).

Prior art of interest includes U.S. Pat. No. 6,960,342 which relates to a *Bacillus amyloliquefaciens* strain that exhibits broad antifungal activity. This disclosure also refers to the use of the *Bacillus amyloliquefaciens* strain or an antifungal composition comprised of the novel strain for control of a broad range of fungal plant pathogens.

U.S. Pat. No. 6,589,524 relates to a biological control composition and method including specific strains of *Bacillus*, which are selected from the group of *Bacillus cereus* NRRL B-30517 and NRRL B-30519, *Bacillus amyloliquefaciens* NRRL B-30518 and *Bacillus subtilis* NRRL B-30520. Here, the specific strains, in combination, provide an effect against pathogenic fungi. The pathogenic fungi include varied *Phytophthora* species such as *P. capsici*.

WO/2005/059112 relates to relates to a *Bacillus amyloliquefaciens* KTGB0202 and a method for controlling plant pathogens using the same. This strain has a control effect against crop powdery mildew and a broad spectrum of antifungal activity against plant pathogenic fungi and inhibits tobacco mosaic virus infection, as well as an eco-friendly bacterial culture broth for controlling powdery mildew, which contains the same.

Prior art of interest also includes U.S. patent application Ser. Nos. 12/511,499, 12/503,272 and 12/492,816 (all of which are herein incorporated by reference in their entirety) referring to *Bacillus amyloliquefaciens* strains NRRL B-50154, NRRL B-50151, and NRRL B-50141, respectively, and compositions and uses of these strains.

*Bacillus amyloliquefaciens* strain SB3200 is included in products sold by Novozymes for cleaning and odor control applications in which enzymes help remove organic soils that cause inorganic soils to cling and promote malodors and for drainline/grease trap applications in which the strain helps degrade grease and organics that cause drainline build-ups that cause blockages.

There is a continuous need to identify strains that are excellent producers and/or secretors of enzymes suitable for industrial use. Further there is a continuous need to identify new strains which produce/secrete multiple useful enzymes and/or have antifungal applications. It is desirous to identify a single strain that can produce excellent amylase, surfactant and amylase activity. The identification of novel strains is needed to solve continuing industrial needs for improving industrial applications in the area of agriculture production, detergent industry, bio-ethanol industry and the baking industry.

SUMMARY OF THE INVENTION

A novel strain of *Bacillus amyloliquefaciens* strain NRRL B-50350 has now been identified and isolated. The strain is characterized as a strain of *Bacillus* bacteria which produces enzymes having excellent amylase, surfactant and antifungal activity. Further, the *Bacillus amyloliquefaciens* strain of the present disclosure has lipase activity, phage resistance, and is tolerant of extreme pH, salt, and extreme temperature. The *Bacillus amyloliquefaciens* strain of the present disclosure and enzymes it produces is useful in a number of applications in the areas of agriculture production, detergent industry, bio-ethanol industry and the baking industry as set forth below.

More specifically, the present disclosure relates to a biologically pure culture of *Bacillus amyloliquefaciens* strain NRRL B-50350. *Bacillus amyloliquefaciens* strain NRRL B-50350 is a bacteriophage-resistant (phage-resistant) strain of *Bacillus amyloliquefaciens*. In order to propagate *Bacillus amyloliquefaciens* strain NRRL B-50350 to a number large enough to allow broad application of this strain, repeated, large-scale fermentation is required. It is known that the natural introduction of native bacteriophage can occur in standard large-scale fermentation systems over repeated growth events or batches. Such an infection can rapidly lead to a complete loss of the culture within hours or days, negating the ability to provide the strain for practical applications. *Bacillus amyloliquefaciens* strain NRRL B-50350 is resistant to such a phage, and therefore maintains growth and realizes the benefits described herein.

*Bacillus amyloliquefaciens* strain NRRL B-50350 is able to produce amylase, which catalyze the degradation of the principal chemical components of drain residues, such as starches.

This present disclosure also relates to a liquid composition comprising *Bacillus amyloliquefaciens* strain NRRL B-50350 in an aqueous solution, e.g., distilled water, tap water, a saline solution or other aqueous solution.

The present disclosure is also directed to a formulation which enhances plant root development and bioaugmentation of plant growth medium.

The present disclosure is also directed to a drain opener formulation comprising *Bacillus amyloliquefaciens* strain NRRL B-50350

The present disclosure also relates to methods of killing fungi by contacting the fungi with *Bacillus amyloliquefaciens* strain NRRL B-50350.

The present disclosure also relates to a liquid formulation which kills fungi comprising *Bacillus amyloliquefaciens* strain NRRL B-50350.

The present disclosure also relates to a method of treating plant seeds comprising contacting seeds with an effective amount of *Bacillus amyloliquefaciens* strain NRRL B-50350.

The present disclosure also relates to a method of treating plant growth medium comprising contacting growth medium with an effective amount of *Bacillus amyloliquefaciens* strain NRRL B-50350.

The present disclosure also relates to a method of killing fungi comprising contacting fungi with an effective amount of *Bacillus amyloliquefaciens* strain NRRL B-50350.

The present disclosure also relates to a method of degrading starch comprising contacting starch with an effective amount of *Bacillus amyloliquefaciens* strain NRRL B-50350.

The present disclosure also relates to a method of altering baking ingredients comprising contacting baking ingredients with an effective amount of *Bacillus amyloliquefaciens* strain NRRL B-50350.

The present disclosure also relates to a method of degrading lipids comprising contacting lipids with an effective amount of *Bacillus amyloliquefaciens* strain NRRL B-50350.

The present disclosure also relates to a method of treating waste water comprising the step of adding to the wastewater the *Bacillus amyloliquefaciens* strain NRRL B-50350.

The present disclosure also relates to method of cleaning a surface comprising the step of contacting the surface with *Bacillus amyloliquefaciens* strain NRRL B-50350.

The present disclosure also relates to a composition comprising the *Bacillus amyloliquefaciens* strain NRRL B-50350. Suitable compositions comprise one or more other microorganisms. In embodiments, suitable compositions comprise one or more surfactants, and/or one or more enzymes. Non-limiting examples of suitable enzymes include one or more alpha-amylases, cellulases, lipases, mannanases, pectate lyases, peroxidases/oxidases, and proteases, or mixtures thereof. In embodiments, compositions further comprises one or more ingredients selected from the group consisting of dispersants, stabilizers, anti-microbial agents, fragrances, dyes, and biocides. In composition embodiments, the *Bacillus amyloliquefaciens* strain NRRL B-50350 is present in a concentration of from about $1 \times 10^5$ to $1 \times 10^{10}$ per ml.

As used herein the term "effective amount" refers to an amount capable of providing a beneficial effect or preventing, alleviating or eliminating an undesirable condition. Non-limiting examples of beneficial effects include improved plant seed quality, improved plant growth medium quality, biocidal effect on fungi population, biostatic effect on fungi population, starch degradation, baking ingredient alteration, lipid degradation, improved waste water quality, improved surface cleanliness, and/or decreased malodor and combinations thereof.

As used herein the word "treat," "treating" or "treatment" refers to using the strain or compositions of the present disclosure either prophylactically to prevent outbreaks of one or more undesirable conditions, or therapeutically to ameliorate one or more existing undesirable conditions. Treatment regimens in accordance with the present disclosure improve plant seed quality, improve plant growth medium quality, reduce and/or eliminate undesirable fungi, and improve the cleanliness of a surface.

These and other aspects of this disclosure will be evident upon reference to the following detailed description.

DETAILED DESCRIPTION OF THE PREFERRED EMBODIMENTS

Figure 1:
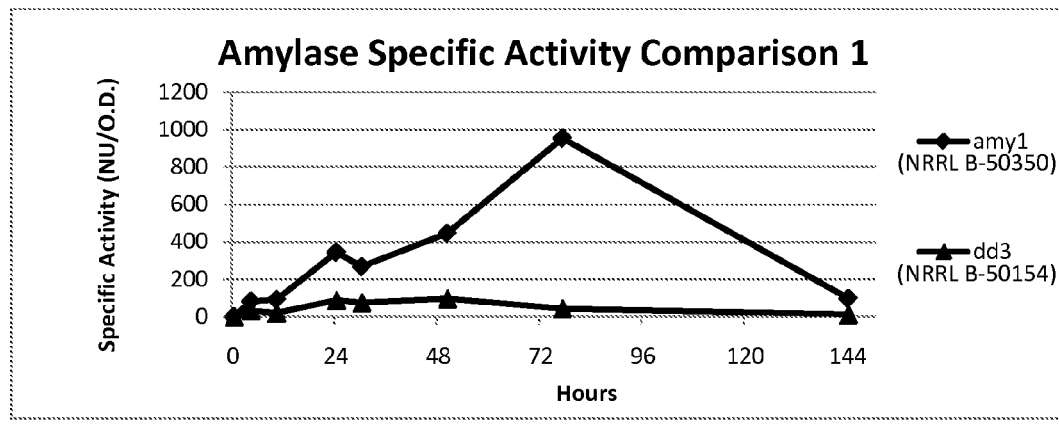
FIG. 1 is a graph showing amylase specific activity over time.

The present disclosure relates to *Bacillus amyloliquefaciens* strain NRRL B-50350. The strain is characterized as *Bacillus* bacteria having excellent amylase, surfactant and/or antifungal activity. Further, the strain of the present disclosure produces multiple useful enzymes and has lipase activity, phage resistance, and high tolerance to salt (e.g. up to 7.5% sodium chloride and temperature (e.g. up to 50° C.). The *Bacillus amyloliquefaciens* strain of the present disclosure and enzymes it produces has a number of applications in the areas of agriculture production, detergent industry, bio-ethanol industry and the baking industry.

In embodiments, the present disclosure relates to a biologically pure culture of *Bacillus amyloliquefaciens* strain NRRL B-50350.

In embodiments, the *Bacillus amyloliquefaciens* strain NRRL B-50350 of the present disclosure is suitable for use in a variety of compositions and methods. Non-limiting examples of suitable compositions of the present disclosure include any composition including *Bacillus amyloliquefa*-

*ciens* strain NRRL B-50350; aqueous solutions containing *Bacillus amyloliquefaciens* strain NRRL B-50350, compositions including *Bacillus amyloliquefaciens* strain NRRL B-50350 and one or more microorganisms; compositions including *Bacillus amyloliquefaciens* strain NRRL B-50350 and surfactant; compositions including *Bacillus amyloliquefaciens* strain NRRL B-50350 and one or more enzymes. Non-limiting enzymes suitable for use in accordance with the present disclosure include alpha-amylases, cellulases, lipases, mannanases, pectate lyases, peroxidases/oxidases, and proteases, or mixtures thereof. Other non-limiting examples of compositions include *Bacillus amyloliquefaciens* strain NRRL B-50350 and one or more dispersants, stabilizers, anti-microbial agents, fragrances, dyes, and biocides.

In embodiments, compositions in accordance with the present disclosure are in liquid form including a water solvent.

It is envisioned that compositions of the present disclosure have *Bacillus amyloliquefaciens* strain NRRL B-50350 present in a concentration of from about $1 \times 10^5$ to $1 \times 10^{10}$ per ml.

Other non-limiting examples of suitable compositions in accordance with the present disclosure include drain opener formulations, sanitizer formulations, or odor neutralizer compositions.

In embodiments, the present disclosure is directed to a drain opener formulation comprising *Bacillus amyloliquefaciens* strain NRRL B-50350 in an aqueous medium. Non-limiting examples of suitable drain opener formulations may further comprise surfactant(s) and/or preservative(s). Drain opener embodiments of the present disclosure have numerous advantages over currently available drain openers; such as activity at pH's closer to neutral, and solubilizing ability for soaps, fats, oils and greases. Embodiments further provide for biological activity specific to carbohydrates, and establishes a biofilm in the drains and on downstream surfaces to continuously aid the natural biodegradative process.

In embodiments, the drain opener formulation includes a stable suspension of viable microorganisms, surfactant(s), preservatives, and optional fragrances in an aqueous medium with a preferred pH of approximately 5 to 6.

An operable concentration range for the microorganisms is from about $1 \times 10^6$ to $1 \times 10^9$ CFU/ml, and in embodiments a concentration of about $1 \times 10^8$ CFU/ml, such as about $1 \times 10^7$ CFU/ml of the formulation.

Unlike typical detergents, which predominately only clean surfaces, the surfactant in formulation embodiments of the present disclosure can solubilize grease and make it bioavailable. The surfactant can be any readily biodegradable surfactant, or a mixture of surfactants with low toxicity for the microorganisms contained within the system. The surfactant(s) should have a high grease solubilizing capability. Ionic surfactants or blends of nonionic/ionic surfactants having a hydrophile/lipophile balance approaching 10 are particularly preferred for the necessary grease solubilization. Non-limiting examples of surfactants suitable for use with the present disclosure include n-alkyl benzene sulfonates and alkyl sulfonates. Non-limiting examples of nonionic surfactants include aliphatic alcohol alkoxylates, alcohol ethoxylates, polyalkylene oxide copolymers, alkyl phenol alkoxylates, carboxylic acid esters, carboxylic amides, and others. In embodiments, surfactant is present in a concentration from about 3 to 10 weight percent of the total composition or formulation.

In drain opener formulation embodiments, the pH of the solution should be maintained as near as possible to neutral to insure adequate bacterial activity, and to minimize health risk, but be in a range compatible for surfactant activity and conducive to the survival of the bacteria. An operable pH range can be between about 3 to 10.

In drain opener formulation embodiments, a preservative such as paraben, methyl paraben, or 1-2-benzisothiazolin-3-one is added to inhibit or prevent the growth of undesirable microbial contaminants in the product. The necessity for a preservative is greatest when the pH is near neutral, and the least when the pH is at the extreme ends of the operable range. The concentration of the preservative is determined by the vendor's recommendations. A typical concentration range for the preservative used in the example is from about 0.075 to 0.75 weight percent of the total composition or formulation.

An additional optional preservative can be added specifically to preserve the spore form of the microorganisms. In embodiments, methyl anthranilate in concentrations of from about 25 to 50 ppm (w/v) by weight is a satisfactory additive.

In drain opener formulation embodiments, optionally a chelating agent is added to enhance stabilization of the formulation.

In drain opener formulation embodiments, a fragrance can optionally be added to mask the odor of the product components, and for market appeal. The fragrance must be compatible with the other components of the formulation.

In embodiments, the present disclosure also relates to sanitizer formulations comprising *Bacillus amyloliquefaciens* strain NRRL B-50350. The formulations comprise a suspension of a sanitizing composition, bacterial spores, and surfactants all contained in an aqueous solution. These formulations have the advantages of being a good surface cleaning agent and a good sanitizer along with providing the long term effect of beneficial bacteria that control pathogens and degrade wastes both on the surface and in the sewage system receiving the surface rinsate.

Sanitizing agents or composition and disinfectants belong to the same category of antimicrobial (active) ingredient. Antimicrobial (active) ingredients are compounds that kill microorganisms or prevent or inhibit their growth and reproduction and that contribute to the claimed effect of the product in which it is included. More specifically, a sanitizer is an agent that reduces the number of microbial contaminants or pathogens to safe levels as judged by public health requirements.

In sanitizer embodiments, the surfactant component functions to clean the surface by removing the soil, dirt, dried urine and soap and helps in sanitizing the surface. The sanitizing composition sanitizes the surface (kills pathogens) and preserves the formulation from contamination by unwanted microorganisms. The bacterial spores and vegetative cells function to seed the waste collection system, control odor and provide a healthy dominant microbial population that inhibits the growth of pathogens through substrate competition, production of antibiotics, etc.

In one sanitizer embodiment of the present disclosure, the composition comprises 1,2-benzisothiazolin-3-one (Proxel), tetrasodium ethylenediaminetetraacetate (EDTA), and isopropyl alcohol (IPA) at a selected range of concentrations, combined with other components of the formula, can effectively inactivate indicator organisms. This sanitizing composition preferably is at neutral pH and does not contain chlorine-related materials, which are commonly used as sanitizers. Consequently, this sanitizing composition is more environmentally friendly and less or not corrosive.

In embodiments, when a sanitizing formulation is applied to a bathroom fixture, sink, toilet bowl, etc., it can be sprayed or squeezed out of a container directly onto a surface or brush.

The formulation is then left on the surface or scoured against the surface with a brush for not less than 10 minutes. The product is then flushed or rinsed with water and discharged from the fixture.

In embodiments, sanitizer formulations of the present disclosure contain sanitizing agents, bacterial spores, and surfactants. Fragrance and dye are also added to control smell and color of the formulations, respectively. Depending on the intended use, the formulation can optionally contain an abrasive. While the key components remain the same, different thickening agents might be used in the formulation with and without an abrasive.

Although many sanitizing agents can be used for inactivating pathogens on surfaces, not all of them can be used in embodiments of the present disclosure. This is because the sanitizing agents used in this present disclosure are not only required to inactivate pathogens effectively, but must not have negative effects on the stability and activity of the bacterial spores contained in the formulation. In addition, the sanitizing agents are required to be relatively friendly to the environment, and should not cause skin sensitization, and should not corrode the construction materials of the fixtures on which they are used.

In embodiments, sanitizing composition of the present disclosure includes Proxel, EDTA, and IPA at selected ranges of concentrations. The maximum concentration of Proxel not likely to cause skin sensitization is about 2,900 mg/L. The suitable concentration ranges of Proxel, Versene (Versene contains 39% EDTA), and IPA for producing a 4 log reduction in the count of an indicator organism in 10 minutes are 0.087 to 0.29% (vol.), 0.36 to 1.19% (vol.), and 3.5 to 7% (vol.), respectively. An additional compound, methyl anthranilate, may also be used in the formulations of the invention. The purpose of using methyl anthranilate is to assist in preservation of the formulations.

In embodiments, sanitizing agents, such as quaternary ammonium compounds (QACs), nitro-containing organosulfur and sulfur-nitrogen compounds, may also be used in the sanitizing compositions of the present disclosure.

In sanitizer embodiments, an operable concentration range for the microorganisms is from $1\times10^5$ to $1\times10^9$ CFU/ml, such as $10^7$ CFU/ml (CFU, colony forming unit) of the formulation.

In embodiments, surfactants are included in the sanitizer formulations of the present disclosure. The surfactants can wet and emulsify soil, including dirt, dried urine, soap, etc., present on a dirty surface. In addition, surfactants aid in the sanitization of the surface. Unlike surfactants usually used for surface cleaning, the surfactants used in the present disclosure have low toxicity for the microorganisms contained within the formulation. In embodiments, a single surfactant or a blend of several surfactants can be used.

Non-limiting examples of surfactants suitable for use in sanitizer embodiments include nonionic surfactants since they provide the desired wetting and emulsification actions and do not significantly inhibit spore stability and activity. Nonionic surfactants are surfactants having no electrical charge when dissolved or dispersed in an aqueous medium. Non-limiting examples of nonionic surfactants include aliphatic alcohol alkoxylates, alcohol ethoxylates, polyalkylene oxide copolymers, alkyl phenol alkoxylates, carboxylic acid esters, carboxylic amides, and others.

Anionic surfactants or mixtures of anionic and nonionic surfactants may also be used in the formulations of the disclosure. Anionic surfactants are surfactants having a hydrophilic moiety in an anionic or negatively charged state in aqueous solution. Non-limiting examples of anionic surfactants suitable for use herein include sulfonic acids, sulfuric acid esters, carboxylic acids, and salts thereof.

In embodiments, compositions of the present disclosure include abrasives that are water-insoluble solid particles. The purpose of using abrasives is to provide deep scouring and cleaning. Depending on the application, abrasives may be optionally used in the formulation of the disclosure. Non-limiting examples of suitable abrasives include calcium carbonate, magnesium carbonate, silica, etc. In embodiments, the abrasives may be present in a mesh size of 80 to 325 mesh (ASTM E 11-70 (1995).

Since the specific gravity of bacterial spores is usually higher than that of water, a thickening agent needs to be used in this disclosure to suspend the spores. Non-limiting examples of suitable aqueous thickening agents include: polyacrylic acid, polystyrene, polyvinyl alcohol, polypropylene, etc. In embodiments, a thickening agent for suspending bacterial spores is polyacrylic acid (e.g., Acrysol TT615 from Rohm and Haas Co.). If an abrasive is used in the formulation, thickening agents in addition to polyacrylic acid might be needed to maintain the suspension of the abrasive.

In embodiments, a fragrance and a dye can be optionally added to mask the odor and to control the color of the product components, respectively, and for market appeal. The fragrance and dye must be compatible with the other components of the formulation.

In embodiments, the present disclosure is also directed to a composition comprising *Bacillus amyloliquefaciens* strain NRRL B-50350 in an aqueous solution. In embodiments, the aqueous solution is designed to provide short- and long-term odor control effects and is environmentally friendly and economical for use.

In embodiments, an operable concentration range for *Bacillus amyloliquefaciens* strain NRRL B-50350 is from about $1\times10^5$ to $1\times10^{10}$ CFU/ml, e.g., from about $1\times10^6$ to $1\times10^8$ CFU/ml. In embodiments, an operable concentration range for *Bacillus amyloliquefaciens* strain NRRL B-50350 is an amount about $1\times10^8$ CFU/ml, or in embodiments about $1\times10^7$ CFU/ml of the formulation.

In embodiments, deodorant compositions of the present disclosure may comprise an odor neutralizer, which is an agent that can rapidly interact, by chemical reactions, with odorous compounds to produce odorless compounds. These agents should not rely on the masking mechanism of a perfume to control odors. In addition, these agents must be safe for use and cost effective. Neutralizers must be compatible with the microbial components.

In one embodiment of the present disclosure, the neutralizer is propylene carbonate, which has the molecular formula $C_4H_6O_3$. Suitable propylene carbonate for use in accordance with the present disclosure is available from commercial vendors such as Huntsman Chemical Corporation.

In combination with other components of the composition, propylene carbonate can effectively reduce odors, including amine and ammonia odors such as trimethylamine, dimethylamine, and ammonia, which are the major target odorous compounds. In addition, propylene carbonate does not inactivate the microbial components even after a long period of contact.

Other odor neutralizing compounds, such as sodium citrate, sodium bicarbonate, and sodium carbonate, may also be used in embodiments of the present disclosure.

In embodiments, the odor neutralizing agent or compound is present in an amount of 1-15 wt. %, such as 2-10 wt. % of the total composition.

In compositions of the present disclosure, other microbial components are suitable for use therein. Viable microorganisms, or mixtures thereof, which are capable of growing on and degrading common domestic, industrial, pet, and animal wastes, capable of surviving the formulations, and compatible with the formulations, and do not produce malodor while performing, may be used in embodiments of the present disclosure.

Non-limiting examples of other microorganisms which can be used in the compositions of the present disclosure include strains of *Alcaligens, Bacillus, Enterobacter, Klebsiella, Lactobacillus, Nitrobacter, Nitrosomonas, Pseudomonas*, and *Streptococcus*, which are known to produce enzymes which are capable of breaking down organic material which can cause odors on carpets or other fibrous materials.

Other ingredients may be used in the compositions of the present disclosure, including surfactants, fragrances, and dyes.

In composition embodiments, surfactants can wet and emulsify insoluble waste materials present in the treated system and inclusion of surfactants in the composition of the disclosure will add to it a cleaning capability. Furthermore, surfactants can be used to break down the insoluble wastes therefore increasing the availability of them to microbial degradation. Suitable surfactants for the disclosure include non-ionic and anionic types. In embodiments, the surfactant is present in an amount of 0-8 wt. %, such as 0-6 wt. % of the composition.

In embodiments, fragrance and dye can be optionally added to mask the odor and to control the color of the composition of the disclosure, respectively, and for market appeal. The fragrance and dye must be compatible with other ingredients of the composition.

It has been found the strain of the present disclosure has very strong surfactant activity. Further, the strain of the present disclosure is suitable for use in controlling pathogenic fungi. One non-limiting example of pathogenic fungi is fungi that produce ooze spore known for causing damping off disease. In embodiments, ooze spore is sensitive to surfactants including the surfactants produced by the strain of the present disclosure. Contacting the ooze spore with the strain of the present disclosure and/or the surfactant has a biocidal and/or biostatic effect on fungi known for making ooze spore. In embodiments, the strain of the present disclosure has excellent antifungal activity against *Pythium* spp. In embodiments, *Bacillus amyloliquefaciens* strain NRRL B-50350 and compositions containing this strain are contacted with seeds and/or a growth medium having undesirable fungi and in need of treatment. *Bacillus amyloliquefaciens* strain NRRL B-50350 has a biocidal effect on the fungi and alleviates the undesirable fungal condition. Accordingly, the seeds and/or plant growth medium is altered and is more suitable for growing plants therein. In embodiments, methods in accordance with the present disclosure are suitable for killing a genus of parasitic oomycete known as *Pythium*.

In embodiments of the present disclosure, the methods and compositions are suitable for use in the detergent area. It has been surprisingly found that the strain of the present disclosure includes very high amylase, surfactant and antifungal activity. For example, the strain of the present disclosure produces excellent amounts of amylase, surfactant, while having excellent antifungal activity against *Pythium* spp. In embodiments, *Bacillus amyloliquefaciens* strain NRRL B-50350 and compositions containing this strain are contacted with a soiled substrate in need of treatment. *Bacillus amyloliquefaciens* strain NRRL B-50350 breaks down starch and starch stains there and alleviates the undesirable unclean condition. Accordingly, the substrate, such as a fabric or surface is altered and is cleaner in appearance.

In embodiments, the strain and compositions including *Bacillus amyloliquefaciens* strain NRRL B-50350 of the present disclosure are suitable for use in a variety of method applications. Non-limiting examples of suitable methods include treating plant seeds by contacting seeds with an effective amount of the *Bacillus amyloliquefaciens* strain of the present disclosure; treating plant growth medium by contacting growth medium with an effective amount of *Bacillus amyloliquefaciens* strain of the present disclosure; killing fungi by contacting fungi with an effective amount of *Bacillus amyloliquefaciens* strain of the present disclosure; degrading starch by contacting starch with an effective amount of *Bacillus amyloliquefaciens* strain of the present disclosure; altering baking ingredients by contacting baking ingredients with an effective amount of *Bacillus amyloliquefaciens* strain of the present disclosure; degrading lipids by contacting lipids with an effective amount of *Bacillus amyloliquefaciens* strain of the present disclosure; treating waste water comprising the step of adding to the wastewater the *Bacillus amyloliquefaciens* strain of the present disclosure; and cleaning a surface by contacting the surface with *Bacillus amyloliquefaciens* strain of the present disclosure. Non-limiting examples of suitable surfaces for cleaning in accordance with the present disclosure include a hard surface, preferably made of one or more materials selected from the group consisting of metal, plastics, rubber, board, glass, wood, paper, concrete, rock, marble, gypsum, and ceramic materials, such as porcelain; or a soft surface, preferably made of one or more materials selected from the group consisting of fibers, e.g., yarns, textiles, vegetable fibers; rock wool, hair; skin; keratinous materials; and internal organs, e.g., lungs; or a porous surface.

In embodiments, the treatment includes the application of an effective amount of one or more strain compositions. Non-limiting examples include drain opener formulations, sanitizer formulations, and odor neutralizer compositions. Such treatments may prevent, alleviate, or eliminate an undesirable condition.

Non-limiting examples of beneficial effects include improved plant seed quality, improved plant growth medium quality, biocidal effect on fungi population, biostatic effect on fungi population, starch degradation, baking ingredient alteration, lipid degradation, improved waste water quality, improved surface cleanliness, and/or decreased malodor and combinations thereof.

Deposit of Biological Material

A *Bacillus amyloliquefaciens* strain was deposited under the terms of the Budapest Treaty on Apr. 12, 2010 with the Agricultural Research Service Culture Collection, 1815 North University Street, Peoria, Ill. 61604, U.S.A., under accession number NRRL B-50350. The deposit shall be maintained in viable condition at the depository during the entire term of the issued patent and shall be made available to any person or entity for non-commercial use without restriction, but in accordance with the provisions of the law governing the deposit.

The following examples are given as exemplary of the disclosure but without intending to limit the same. In order that those skilled in the art may be better able to practice the compositions and methods described herein, the following examples are given as an illustration of the preparation of the present compositions and methods. It should be noted that the disclosure is not limited to the specific details embodied in the examples.

EXAMPLES

Example 1

Materials & Methods

*Bacillus amyloliquefaciens* strain NRRL B-50350 ("Strain SB3778") was isolated from a research lab area. Studies were conducted including: a bacterial identification study; DNA fingerprint study; bio-surfactant activity study; antifungal activity study; stress tolerance study; proteinase activity study; and gene clone for amylase.

Isolation and Identification of *Bacillus amyloliquefaciens* Strain NRRL B-50350

A 1600 base full length 16s DNA was obtained from *Bacillus amyloliquefaciens* strain NRRL B-50350 isolate and the sequence was analyzed. The analysis identified the bacterial isolate as *Bacillus amyloliquefaciens*.

*Bacillus amyloliquefaciens* Strain NRRL B-50350 has Unique Morphology on SM Plate:

*Bacillus amyloliquefaciens* strain NRRL B-50350 was compared with known strains of *Bacillus amyloliquefaciens*. Specifically, growth and morphology were compared. *Bacillus amyloliquefaciens* strain NRRL B-50350 was morphologically different from all other *Bacillus amyloliquefaciens* strains on SM medium. All other *B. amyloliquefaciens* strains produced exopolysaccharides on SM agar plate and *Bacillus amyloliquefaciens* strain NRRL B-50350 did not.

*Bacillus amyloliquefaciens* Strain NRRL B-50350 has a Unique Genotype

*Bacillus amyloliquefaciens* strain NRRL B-50350 was compared with known strains of *Bacillus amyloliquefaciens* by way of DNA fingerprinting analysis. The results demonstrated *Bacillus amyloliquefaciens* strain NRRL B-50350 had 70% similarity to a known strain of *Bacillus amyloliquefaciens*.

*Bacillus amyloliquefaciens* Strain NRRL B-50350 Produced More Amylase Activity than Well-Known Strain of *Bacillus amyloliquefaciens* for Amylase Production in House:

*Bacillus amyloliquefaciens* strain NRRL B-50350 was evaluated for amylase activity against known strain of *Bacillus amyloliquefaciens* known to be amylase producer, i.e., DD3, having the deposit accession number NRRL B-50154. Amylase activity was determined with Konelab KNU-B analysis using BAN. In this procedure alpha-amylases (1,4-α-D-glucanohydrolases, E.C. 3.2.1.1) catalyze the hydrolytic degradation of polymeric carbohydrates such as amylose, amylopectin and glycogen by cleaving 1,4-alpha-glucosidic bonds. In polysaccharides and oligosaccharides, several glycosidic bonds are hydrolyzed simultaneously. Maltotriose, the smallest such unit, is converted into maltose and glucose, albeit very slowly. The kinetic method described here is based on the well-proven cleavage of 4,6-ethylidene-(G7)-1,4-nitrophenyl-(G1)-α,D-maltoheptaoside by alpha-amylase and subsequent hydrolysis of all the degradation products to p-nitrophenol with the aid of alpha-glucosidase. This results in 100% liberation of the chromophore.

This process has been automated in the Konelab Arena 30 with the following steps: 1) 200 microliters of R1 reagent is pipetted into cuvette, 2) 16 microliters of sample is added to cuvette, 3) Mixture is incubated for 300 seconds to obtain temperature of 37.degree. C., 4) 20 microliters of R2 reagent is pipetted into cuvette and mixture is incubated for 180 seconds, and 5) Absorption is measured every 18 seconds at 405 nm for a total of 7 measurements for each sample.

Defined oligosaccharides were cleaved under the catalytic action of alpha-amylases. The resulting PNP derivatives are cleaved directly to PNP by the action of alpha-glucosidase and the color intensity of the p-nitrophenol formed is directly proportional to the alpha-amylase activity and is measured spectrophotometrically.

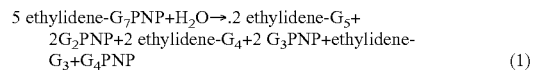

$$5 \text{ ethylidene-}G_7PNP + H_2O \rightarrow .2 \text{ ethylidene-}G_5 + 2G_2PNP + 2 \text{ ethylidene-}G_4 + 2 G_3PNP + \text{ethylidene-}G_3 + G_4PNP \quad (1)$$

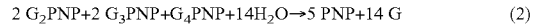

$$2 G_2PNP + 2 G_3PNP + G_4PNP + 14 H_2O \rightarrow 5 PNP + 14 G \quad (2)$$

Reaction (1) was mediated by the amylase added from the standard or sample. Reaction (2) was mediated by the glucosidase provided in the kit. The results proved that amylase activity from *Bacillus amyloliquefaciens* strain NRRL B-50350 was at least 5 times more than known strain i.e., DD3 (strain NRRL B-50154).

Enzyme Analysis: For each strain, a single colony was inoculated into 10 mL PCB media and left overnight. Approximately $1 \times 10^4$ cells of each strain were inoculated into 100 mL starch media. O.D. readings were taken at each time point specified in the graphs below. For each strain at each time point, 2 mL of cell-free supernatant material was combined with 1 mL 50% glycerol and stored at −20° C. The enzyme activity for all samples was determined by Konelab KNU-B analysis using BAN as described previously. A repeat of this procedure was performed for result confirmation.

Referring now to FIG. 1, the study yielded approximately a five-fold increase in amylase production in amy1 (strain NRRL B-50350) when compared with DD3 (strain NRRL B-50154).

Figure 2:
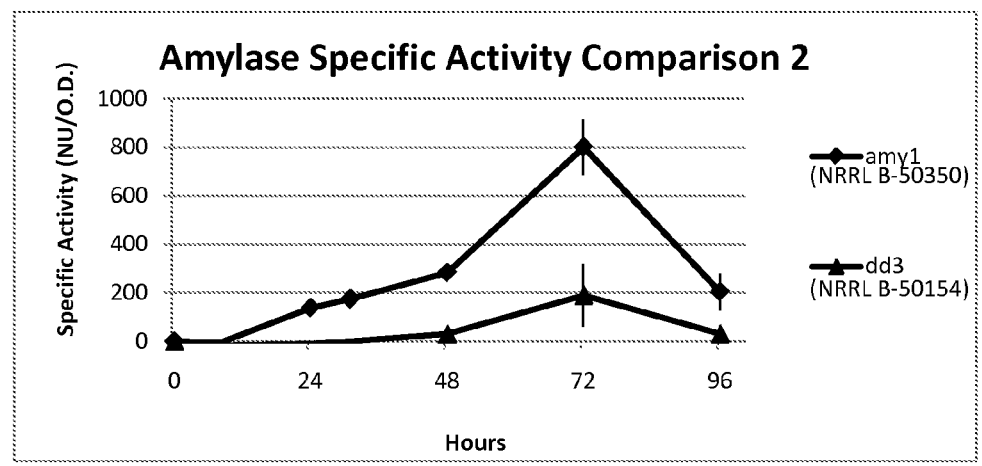
FIG. 2 is a graph showing amylase specific activity over time.

A second trial resulted in a four-fold increase in amylase production when amy1 (strain NRRL B-50350) was compared to DD3 (strain NRRL B-50154). These results are shown in FIG. 2. Throughout both studies, strain NRRL B-50350 consistently outperformed a standard strain in amylase production with a maximum amylase production for strain NRRL B-50350 about 800 NU.

Units Defined

BAN is an alpha-amylase available from Novozymes. The analytical standard was supplied at 360 KNU(B)/g=360 NU(B)/mg.

*Bacillus amyloliquefaciens* Strain NRRL B-50350 has Protease and Lipase Activity.

The protease assay was set up as per the protocol described for the amylase assay above. Konelab analysis was performed as follows:

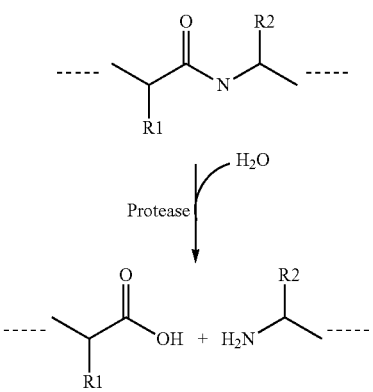

Proteases hydrolyze DMC (N,N-dimethylcasein). When the peptide bond is hydrolyzed, a carboxylic acid and primary amine are formed as two new ends of the oligopeptide. The primary amine then reacts under alkaline conditions with trinitrobenzene sulfonic acid (TNBS) to form a colored complex:

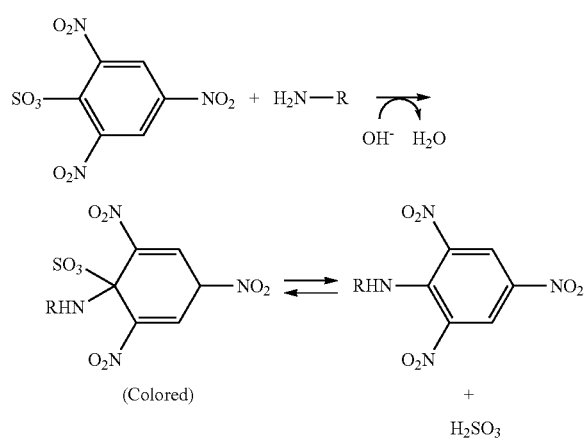

The colored complex is detected at 405 nm kinetically in the Konelab Arena 30 using the following procedure: 1) 180 microliters of DMC solution is pipetted into the cuvette, 2) Mixture is incubated for 480 seconds to obtain temperature of 50° C., 3) 36 microliters of TNBS is pipetted into the cuvette and mixed, 4) Mixture is incubated for 60 seconds to regain a temperature of 50° C., 5) 18 microliters of sample is pipetted into the cuvette and mixed, 6) Mixture is incubated for 120 seconds and absorption at 405 nm is measured every 18 seconds for a total of 7 measurements. The reaction between the primary amines and the TNBS is assumed to be faster than the cleavage of DMC, so that the reaction in the presence of excess substrate can be assumed to be a function of the enzyme concentration only.

Figure 3:
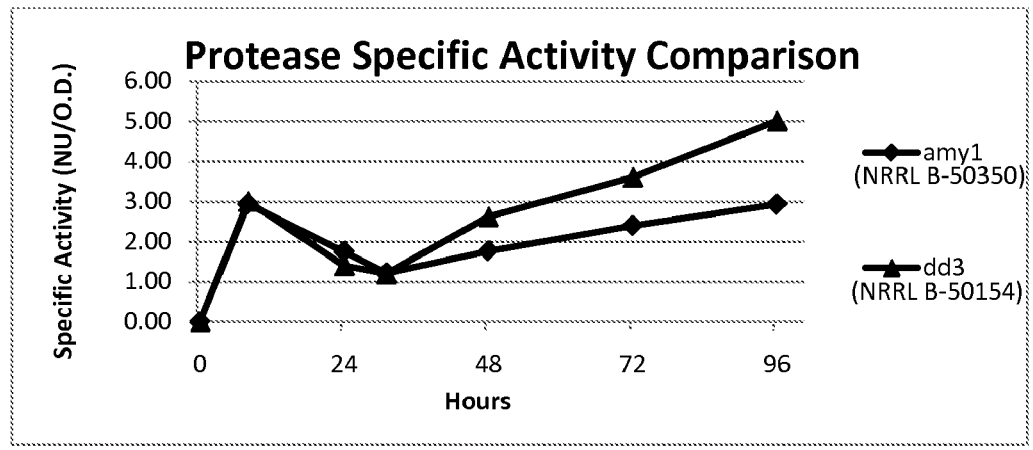
FIG. 3 is a graph showing protease specific activity over time.

Referring to FIG. 3, protease specific activity comparison is provided. *Bacillus amyloliquefaciens* amy1 (strain NRRL B-50350) produces about the same amount of protease as DD3 (strain NRRL B-50154).

The lipase assay was set up as per the protocol described for the amylase assay above. Konelab analysis was performed as follows:

Lipases are special classes of esterase enzymes. Lipases are commonly associated with the breakdown of triglycerides into glycerol and 3 fatty acids. Sometimes lipases will be specific for triglycerides containing fatty acids of a particular chain length, or in other cases be specific for the positional chemistry of the fatty acid on the glycerol moiety. Lipases tend to function at the water-oil interface. In the reaction described here, a p-nitrophenol derivative of a fatty acid is used a substrate for a lipase. There are several fatty acid chain lengths to choose from that are available for this laboratory assay. These include:

pNP-butyrate: $C_4$ pNP-valerate: $C_5$ pNP-palmitate: $C_{16}$ pNP-Valerate is the substrate most commonly used for this assay. The substrate is colorless, while the cleavage product p-nitrophenol has a strong absorption at 405 nm. Therefore enzymatic activity can be followed by monitoring the increase in $A_{405}$ over time. The reaction scheme is shown below:

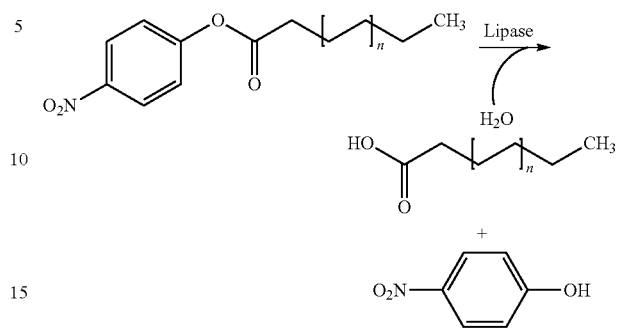

The colored complex is detected at 405 nm kinetically in the Konelab Arena 30 using the following procedure: 1) 175 microliters of pNP-valerate solution is pipetted into the cuvette, 2) Mixture is incubated for 480 seconds to obtain temperature of 37° C., 3) 50 microliters of sample is pipetted into the cuvette and mixed, 4) Mixture is incubated for 250 seconds to regain a temperature of 37° C., 5) Mixture is incubated for 600 seconds and absorption at 405 nm is measured every 54 seconds for a total of 12 measurements.

Figure 4:
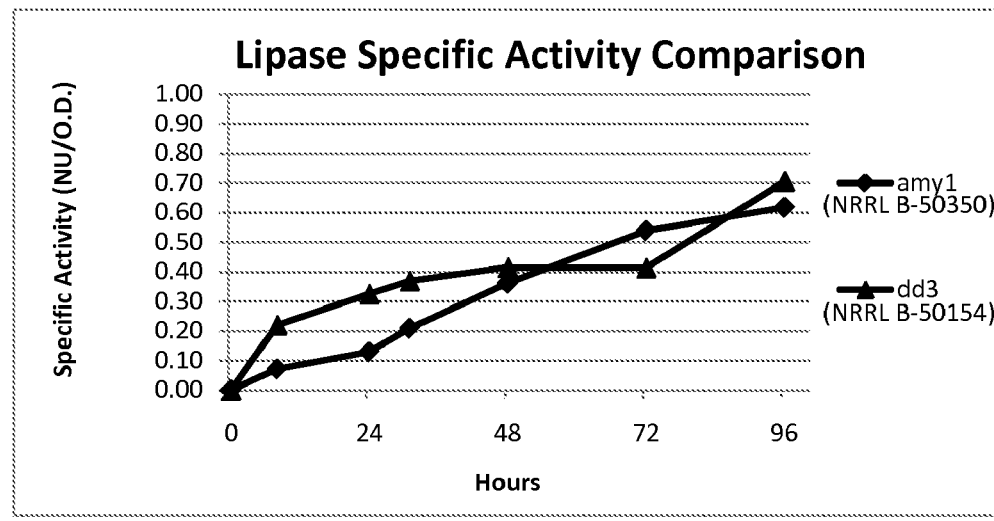
FIG. 4 is a graph showing lipase specific activity over time.

Referring to FIG. 4, *Bacillus amyloliquefaciens* amy 1 (strain NRRL B-50350) produces about the same amount of lipase as DD3 (strain NRRL B-50154).

*Bacillus amyloliquefaciens* Strain NRRL B-50350 has Antifungal Activity:

Antifungal capabilities of strain NRRL B-50350 were compared to those of DD3 (strain NRRL B-50154). Per strain, DD3 (strain NRRL B-50154) inhibited *Pythium* but more strongly inhibited *R. solani* and *S. sclerotiorum*. Strain NRRL B-50350 inhibited all three fungi, most strongly on *Pythium*. In comparison, DD3 (strain NRRL B-50154) was more effective than strain NRRL B-50350 at inhibiting *R. solani* and *S. sclerotiorum*, however, strain NRRL B-50350 inhibited *Pythium* much more strongly than DD3 (strain NRRL B-50154). The data is particularly interesting because it is difficult to find good *Pythium* inhibitors. The results are shown in Table 1 below:

TABLE 1

| Diameter of Inhibition Zones (mm) (data from SSGN) | | | | |
|---|---|---|---|---|
| Check (no inhibition) | | *Pythium* 90.0 mm | *R. solani* 90.0 mm | *S. sclerotiorum* 90 mm |
| Wildtype dd3 (strain NRRL B-50154) | 1 | 5.0 × 5.0 | 20 × 12 | 25 × 10.0 |
|  | 2 | 5.0 × 3.0 | 19 × 13 | 25 × 8.0 |
|  | 3 | 5.0 × 4.0 | 20 × 13 | 25 × 10.0 |
| strain NRRL B-50350 | 1 | 15 × 15.0 | 10 × 10.0 | 10 × 10.0 |
|  | 2 | 15 × 13.0 | 8 × 10.0 | 10 × 11.0 |
|  | 3 | 10 × 10.0 | 10 × 9.0 | 10 × 10.0 |

Example 2

Temperature Tolerance

Method: *Bacillus amyloliquefaciens* strain NRRL B-50350 and an in-house strain (used as a control for comparison) were inoculated into PCB and grown overnight at each of following temperatures: 35° C., 40° C., 45° C., and 50° C. Tolerance was measured by the presence or absence of growth.

Results: Growth was visible up to 50° C. for each strain. Accordingly, the strain of the present disclosure is heat tolerant.

Example 3

Salinity Tolerance

Method: *Bacillus amyloliquefaciens* strain NRRL B-50350 and an in-house strain (used as a control for comparison) were inoculated into bactotryptone (10 g/L) yeast extract (5 g/L) media with the following salt concentrations: 2%, 5%, 7.5%, 10%, and 12.5%. Tolerance was measured by the presence or absence of growth.

Results: Growth was visible up to 7.5% for *Bacillus amyloliquefaciens* strain NRRL B-50350 while control displayed growth up to 12.5%.

Example 4

Biosurfactant Activity

Method: *Bacillus amyloliquefaciens* strain NRRL B-50350 ("amy1" and formerly referred to as "Strain X") and another *Bacillus amyloliquefaciens* strain NRRL B-50017 ("SB3195" and formerly referred to as "Strain Y") with known biosurfactant activity were inoculated into 100 mL of biosurfactant media so that each flask had an O.D. of 0.001. The surface tension and the O.D. were measured at 8, 24, 56, and 72 hours. At 56 hours, various dilutions were performed to determine the biosurfactant strength for amy1 and SB3195.

Figure 5:
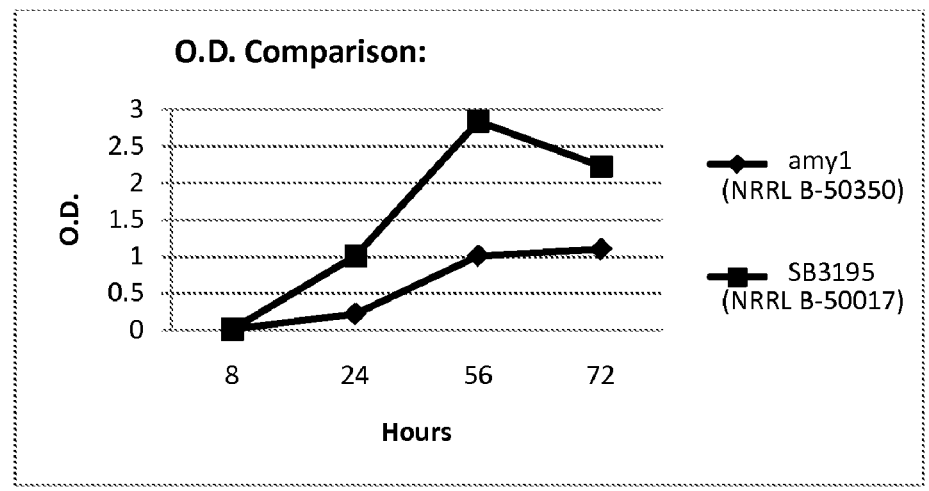
FIG. 5 is a graph comparing biosurfactant production of two strains of *Bacillus amyloliquefaciens*.
Figure 6:
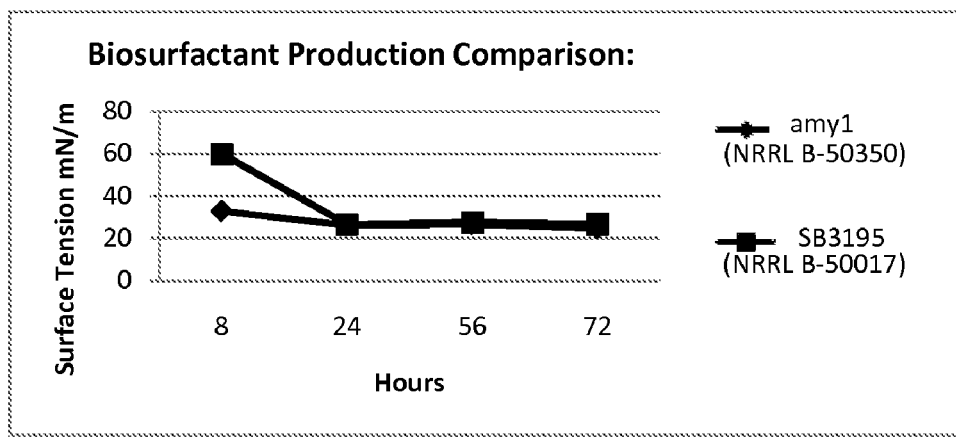
FIG. 6 is a graph comparing biosurfactant production between two strains of *Bacillus amyloliquefaciens*.
Figure 7:
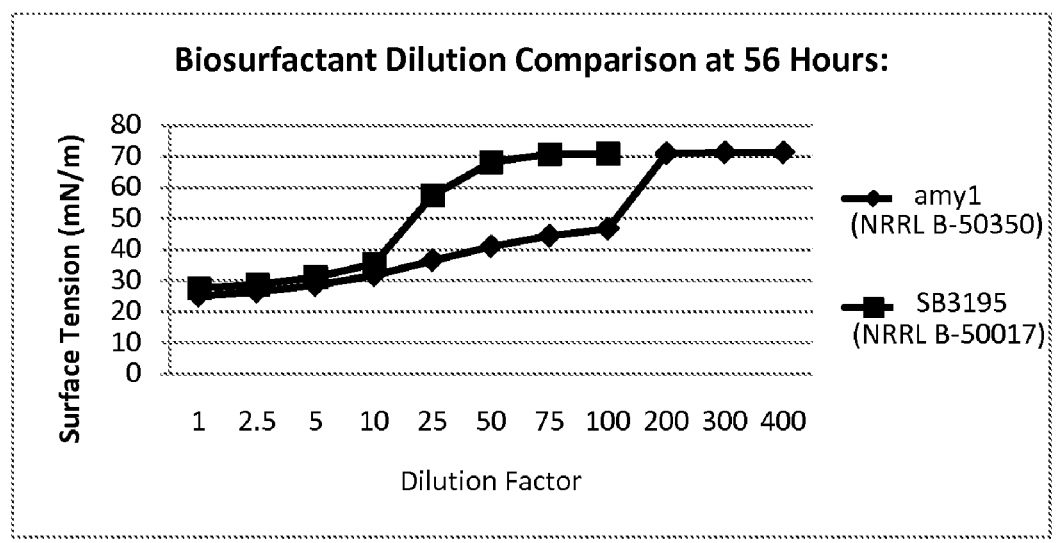
FIG. 7 is a graph comparing surface tension over dilution factor between two strains of *Bacillus amyloliquefaciens*.

Results: Although amy1 and SB3195 were inoculated at the same rate, SB3195 exhibited faster growth than amy1 (FIG. 5). At 56 hours SB3195 growth was 3 times higher than amy1. However, the biosurfactant production for amy1 began at 8 hours while SB3195 exhibited biosurfactant production at 24 hours (FIG. 6). Good biosurfactant activity was determined by a surface tension of less than 50 mN/m. The biosurfactant produced by amy1 could be diluted 100-fold before losing biosurfactant activity while SB3195 lost biosurfactant activity at the 25-fold dilution (FIG. 7). While amy1 exhibited ⅓ the growth of SB3195, amy1 produced a biosurfactant 4 times stronger in terms of dilution than SB3195.

The present invention is described by the following numbered paragraphs:

1. A biologically pure culture of *Bacillus amyloliquefaciens* strain NRRL B-50350.
2. A method of treating plant seeds comprising contacting seeds with an effective amount of *Bacillus amyloliquefaciens* strain of paragraph 1.
3. A method of treating plant growth medium comprising contacting growth medium with an effective amount of *Bacillus amyloliquefaciens* strain of paragraph 1.
4. A method of killing fungi comprising contacting fungi with an effective amount of *Bacillus amyloliquefaciens* strain of paragraph 1.
5. A method of degrading starch comprising contacting starch with an effective amount of *Bacillus amyloliquefaciens* strain of paragraph 1.
6. A method of altering baking ingredients comprising contacting baking ingredients with an effective amount of *Bacillus amyloliquefaciens* strain of paragraph 1.
7. A method of degrading lipids comprising contacting lipids with an effective amount of *Bacillus amyloliquefaciens* strain of paragraph 1.
8. A method of treating waste water comprising the step of adding to the wastewater the *Bacillus amyloliquefaciens* strain of paragraph 1.
9. A method of cleaning a surface comprising the step of contacting the surface with *Bacillus amyloliquefaciens* strain of paragraph 1.
10. The method of paragraph 9, wherein the surface is a hard surface, such as one or more materials selected from the group consisting of metal, plastics, rubber, board, glass, wood, paper, concrete, rock, marble, gypsum, and ceramic materials, such as porcelain; or a soft surface, such as made of one or more materials selected from the group consisting of fibers, e.g., yarns, textiles, vegetable fibers; rock wool; hair; skin; keratinous materials; and internal organs, e.g., lungs; or a porous surface.
11. The method of any of paragraphs 9-10, wherein the method is repeated periodically.
12. The method of any of paragraphs 9-11, comprising contacting the surface with an enzyme, such as an enzyme selected from the group of alpha-amylases, cellulases, lipases, mannanases, pectate lyases, peroxidases/oxidases, and proteases, or mixtures thereof.
13. The method of any of paragraphs 9-12, further comprising subjecting the surface to one or more agents selected from the group consisting of dispersants, surfactants, anti-microbial agents, and biocides.
14. A composition comprising the *Bacillus amyloliquefaciens* strain of paragraph 1.
15. A composition in accordance with paragraph 14 further comprising one or more other microorganisms.
16. The composition of paragraph 14, which further comprises a surfactant.
17. The composition of paragraph 16, which further comprises one or more enzymes.
18. The composition of paragraph 17, wherein the enzyme is selected from the group consisting of alpha-amylases, cellulases, lipases, mannanases, pectate lyases, peroxidases/oxidases, and proteases, or mixtures thereof.
19. The composition of paragraph 14, which further comprises one or more ingredients selected from the group consisting of dispersants, stabilizers, anti-microbial agents, fragrances, dyes, and biocides.
20. The composition of paragraph 14, wherein *Bacillus amyloliquefaciens* strain NRRL B-50350 is present in a concentration of from about $1 \times 10^5$ to $1 \times 10^{10}$ per ml.
21. An isolated microorganism of the strain *Bacillus* NRRL B-50350.

It will be understood that various modifications may be made to the embodiments disclosed herein. Therefore, the above description should not be construed as limiting, but merely as exemplifications of embodiments. Those skilled in art will envision other modifications within the scope and spirit of the claims appended hereto.

The invention claimed is:

1. A biologically pure culture of *Bacillus amyloliquefaciens* strain NRRL B-50350 having phage resistance.
2. A method of killing fungi comprising contacting fungi with an effective amount of *Bacillus amyloliquefaciens* strain of claim 1.
3. A composition comprising the *Bacillus amyloliquefaciens* strain of claim 1.
4. A composition in accordance with claim 3 further comprising one or more other microorganisms.
5. The composition of claim 3, which further comprises a surfactant.

6. The composition of claim 5, which further comprises one or more enzymes.

7. The composition of claim 6, wherein the enzyme is selected from the group consisting of alpha-amylases, cellulases, lipases, mannanases, pectate lyases, peroxidases/oxidases, and proteases, or mixtures thereof.

8. The composition of claim 3, which further comprises one or more ingredients selected from the group consisting of dispersants, stabilizers, anti-microbial agents, fragrances, dyes, and biocides.

9. The composition of claim 3, wherein *Bacillus amyloliquefaciens* strain NRRL B-50350 is present in a concentration of from about $1 \times 10^5$ to $1 \times 10^{10}$ per ml.

* * * * *